United States Patent [19]

Makosza et al.

[11] Patent Number: 5,262,539
[45] Date of Patent: Nov. 16, 1993

[54] PROCESS FOR THE PREPARATION OF AROMATIC AMINES

[75] Inventors: Mieczyslaw Makosza, Warszawa; Maciej Bialecki, Katowice, both of Poland

[73] Assignee: Bayer Aktiengesellschaft, Leverkusen, Fed. Rep. of Germany

[21] Appl. No.: 682,820

[22] Filed: Apr. 9, 1991

[30] Foreign Application Priority Data

Apr. 23, 1990 [PL] Poland ................... 284896

[51] Int. Cl.$^5$ ........................... C07D 213/72
[52] U.S. Cl. .................... 546/307; 546/152; 546/159; 546/304; 548/557; 548/558; 549/29; 549/68; 549/480; 549/481; 558/418; 564/395; 564/408
[58] Field of Search ............ 564/395, 102, 408; 558/418; 549/480, 481, 29, 68; 548/557, 558; 546/304, 152, 159, 307; 562/434, 435, 437

[56] References Cited

U.S. PATENT DOCUMENTS

| | | | |
|---|---|---|---|
| 2,750,417 | 6/1956 | Closson et al. | 564/408 |
| 4,140,853 | 2/1979 | Vorbrueggen | 546/304 |
| 4,386,209 | 5/1983 | McGill et al. | 546/304 |
| 4,950,673 | 8/1990 | Bochis et al. | 546/159 |

OTHER PUBLICATIONS

Mukaiyama et al., Tetrahedron letters, No. 39, 1970, 3411–3414.
Katritzky et al., "Alkylaminonitrobenzenes by Vicarious...", J. of Org. Chem., vol. 53, No. 17 (Aug. 1988), pp. 3978–3982.
Price et al., "4-Nitro-1-Naphthylamine", Organic Syntheses Collective Volume, No. 3, 1955, p. 664.
Padwa et al., "Direct Amination of Nitrobenzenes by Viacarious...", J. of Org. Chem., vol. 51, No. 25, (Dec. 1986), pp. 5038–5040.

Primary Examiner—Glennon H. Hollrah
Assistant Examiner—Shailendra Kumar
Attorney, Agent, or Firm—Sprung Horn Kramer & Woods

[57] ABSTRACT

Electrophilic aromatic compounds can be reacted with sulphenamides in the presence of bases to form the corresponding aromatic amines.

4 Claims, No Drawings

PROCESS FOR THE PREPARATION OF AROMATIC AMINES

The invention relates to a process for the preparation of aromatic amines by the amination of electrophilic aromatic compounds with sulphenamides.

Aromatic amines are important intermediates for the production of dyestuffs, plant protection products and pharmaceuticals and for the photochemical industry.

The method most frequently used for the preparation of aromatic amines is the reduction of the nitro groups of readily obtainable nitroaromatic compounds. The reaction of halogenated aromatic compounds with ammonia or amines also produces aromatic amines. Although these processes are extensively used in industry the yields are frequently not satisfactory due to the multi-step reaction.

The direct amination of various heterocyclic aromatic compounds, in particular quinoline and pyridine, with the aid of an alkali metal amide, preferably sodium amide, is also known (Chichibabin synthesis). Unfortunately the use of this process is limited to a small number of heterocyclic compounds. Amination reactions of nitroaromatic compounds with hydroxylamine (C. C. Price and S. T. Voong, Org. Synth. Coll. Vol. III (1955) 664) and with 4-amino-1,2,4-triazole (A. R. Katrizky and K. S. Laurenzo, J. Org. Chem. 51 (1986) 5039 and 53 (1988) 3978) are also known. These reactions are, however, limited to specific compounds and/or produce yields which are not satisfactory.

Surprisingly a universally applicable process has now been found for the direct amination of electrophilic aromatic compounds: By reacting the latter with sulphenamides aromatic amines are produced directly and in good yields.

The invention thus relates to a process for the preparation of aromatic amines of the formula

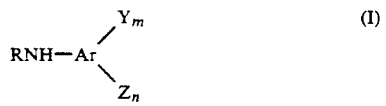

wherein
Ar denotes a mono- or polycyclic, preferably mono- or bicyclic, aromatic radical with 4 to 16 C atoms which can also contain 1 to 2 hetero atoms from the series comprising nitrogen, oxygen and sulphur,
R denotes hydrogen, $C_1$–$C_4$-alkyl(optionally substituted by halogen or $C_1$–$C_4$-alkoxy), $C_1$–$C_4$-alkenyl, $C_5$–$C_{12}$-cycloalkyl, $C_5$–$C_{12}$-aryl(optionally substituted by halogen, $C_1$–$C_4$-alkyl or $C_1$–$C_4$-alkoxy), or $C_2$–$C_6$-acyl,
Y denotes nitro in the 2 or 4 position in relation to the amino group —NHR,
Z denotes halogen, such as fluorine, chlorine, bromine or iodine; cyano; $C_1$–$C_4$-alkyl such as methyl, ethyl or isopropyl; halogenated $C_1$–$C_4$-alkyl such as trifluoromethyl or dichorofluoromethyl; $C_1$–$C_4$-alkoxy such as methoxy and ethoxy; (optionally halogenated) $C_1$–$C_4$-alkylmercapto such as methylmercapto and trifluoromethylmercapto; di-$C_1$–$C_4$-alkylamino such as dimethylamino and diethylamino; $C_1$–$C_4$-alkylsulphonyl such as methylsulphonyl; or carboxyl or hydroxyl and
m denotes 1 or 2 and
n denotes zero, 1 or 2.

As far as the substituents mentioned under Z are concerned, where n=2 the two substituents Z do not have to be identical.

The process according to the invention is carried out in such a manner that compounds of the formula

wherein
Y denotes nitro and the remaining symbols have the abovementioned meaning,
are reacted with organic sulphenamides.

Starting compounds (II) which are preferably to be used for the process according to the invention contain at least one nitro group per molecule.

In formula (I) Ar denotes an (m+n+1)-valent and in formula (II) an (m+n)-valent radical, preferably a benzene, naphthalene, pyridine, quinoline or thiophene radical.

Preferred starting compounds (II) thus comprise o-chloronitrobenzene, m-nitrobenzonitrile, m-trifluoromethyl nitrobenzene, 1- and 2-nitronaphthalenes, 2- and 3-nitrothiophenes, 2-nitrofurans, N-alkylated and N-arylated 2- and 3-nitropyrroles, 2-, 3- and 4-nitropyridines, 4-ethoxy-3-nitropyridine and 5-, 6- and 8-nitroquinolines.

The organic sulphenamides which can be used are practically all the available stable sulphenamides, i.e. all the available stable compounds containing at least one —NH—S— group per molecule. Preferred sulphenamides include, for example, benzthiazyl-2-sulphenamide, N-phenyl-benzenesulphenamide, benzthiazyl-2-cyclohexylsulphenamide, benzthiazyl-2-tert.-butylsulphenamide, N,N-dimethyl- and N,N-diethyl-thiocarbamoyl-sulphenamide and N,N-tetramethylene-thiocarbamoyl-sulphenamide.

The molar ratio of starting compound II/sulphenamide is in general 0.8 to 1.2, preferably 0.9 to 1.1 and in particular about 1:1.

It is assumed that the reaction proceeds according to the following mechanism: The sulphenamide anion formed by the abstraction of a hydrogen atom located on the nitrogen atom forms, together with the aromatic compound II, an adduct from which HSX is then eliminated by the action of a base. It can thus be assumed that the reaction can only take place if basic agents are present.

Preferred basic agents include for example alkali metal hydroxides, alkali metal hydrides, alkali metal amides and alkali metal $C_1$–$C_4$-alcoholates such as, for example, sodium and potassium hydroxide, sodium hydride, sodium amide, lithium diisopropylamide, sodium methylate, sodium ethylate and potassium tert.-butylate.

The basic agent will generally be used in a quantity of at least 2 mols, preferably 2 to 7 mols, in particular 2 to 3.5 mols, per mol of starting compound II or per mol of sulphenamide (if the starting compound II and the sulphenamide are not used in an equimolar ratio: based on the substoichiometric component).

The process according to the invention can be carried out in liquid ammonia or in aprotic organic solvents. Preferred aprotic organic solvents include for example dimethylformamide, dimethyl sulphoxide, tetrahydrofuran, dimethoxyethane, toluene and mixtures thereof.

In the amination according to the invention the amino group —NHR usually enters the p-position (in relation to substituent Y). If the p-position is already occupied the amino group is generally directed towards the o-position. In some cases it is also possible to direct the amino group —NHR into the required position by the appropriate selection of the reaction conditions, in particular of the solvent and the basic agent: Thus, for example, the reaction of N,N-tetramethylenethiocarbamoylsulphenamide with 1-nitronaphthalene in dimethyl sulphoxide in the presence of potassium hydroxide leads to substitution in the 4-position, whereas the reaction of benzthiazyl-2-sulphenamide with 1-nitronaphthalene in dimethylformamide in the presence of potassium tert.-butylate leads to substitution in the 2-position.

The process according to the invention can be carried out at temperatures of $-50°$ to $+100°$ C., preferably $-35°$ to $+30°$ C.

The reaction on which the process according to the invention is based is complete after a period ranging from a few minutes up to several hours, depending, inter alia, on the reaction temperature, the reactivity of the compounds employed and the quantities of the starting ingredients. The progress of the reaction can for example be monitored by thin-layer chromatography.

When the reaction has ended the reaction mixture can be poured into water possibly containing a dissolved salt, e.g. sodium chloride or ammonium chloride, in order to reduce the solubility of amines I in the aqueous phase. From the organic phase the aromatic amines can then be isolated in a manner known per se. Further purification can then be carried out by recystallisation and/or chromatographic purification.

EXAMPLES

All percentages are percentages by weight

Example 1

Preparation of 4-nitro-1-naphthylamine:

3.5 g of 1-nitronaphthalene and 3.3 g of N,N-tetramethylenethiocarbamoylsulphenamide, dissolved in 15 ml of dimethyl sulphoxide, are added dropwise to a vigorously stirred suspension of 6 g of potassium hydroxide in 50 ml of dimethyl sulphoxide, the temperature being kept at 20° to 25° C. When the addition has ended the mixture is stirred for a further 60 minutes, poured into 400 ml of a saturated aqueous ammonium chloride solution and extracted with methylene chloride. After drying and removing the solvent, 4-nitro-1-naphthylamine is obtained with a melting point of 190° to 192° C. The yield is 2.9 g (77%). 1Nitro-2-napthylamine is additionally obtained in a yield of about 2%.

Example 2

Preparation of 1-nitro-2-naphthylamine:

3.5 g of 1-nitronaphthalene and 3.7 g of benzthiazyl-2-sulphenamide, dissolved in 30 ml of dimethylformamide, are added dropwise to a stirred solution of 6 g of potassium tert.-butylate in 60 ml of dimethylformamide, while the temperature is kept at 20° to 25° C. After stirring further for 15 minutes the mixture is poured into 400 ml of a saturated aqueous ammonium chloride solution and then treated further as in Example 1. 1-Nitro-2-naphthylamine with a melting point of 123° to 125° C. is obtained in a yield of 2.9 g (72%). In addition, about 8% of 4-nitro-1-naphthylamine are obtained.

Example 3

Preparation of 3-chloro-4-nitroaniline:

3-Chloro-4-nitroaniline with a melting point of 156° to 159° C. is obtained in a yield of 0.25 g (72%) from 0.32 g of o-chloronitrobenzene, 0.33 g of N,N-tetramethylenethiocarbamoylsulphenamide and 0.6 g of potassium tert.-butylate following the same procedure as in Example 2.

Example 4

Preparation of 2-amino-5-nitrobenzonitrile:

2-Amino-5-nitrobenzonitrile with a melting point of 202° to 204° C. is obtained from 0.3 g of m-nitrobenzonitrile, 0.33 g of N,N-tetramethylenethiocarbamoylsulphenamide and 0.6 g of powdered potassium hydroxide following the same procedure as in Example 1. The yield is 0.26 g (78%).

Example 5

Preparation of N-phenyl-4-nitro-1-naphthylamine:

N-Phenyl-4-nitro-1-naphthylamine with a melting point of 158° C. is obtained from 0.35 g of 1-nitronaphthalene, 0.4 g of N-phenylbenzenesulphenamide and 0.6 g of powdered potassium hydroxide following the same procedure as in Example 1; the yield is 0.32 g (61%).

Example 6

Preparation of 2-amino-4-ethoxy-5-nitropyridine:

2-Amino-4-ethoxy-5-nitropyridine with a melting point of 215° to 217° C. is obtained from 0.34 g of 4-ethoxy-3-nitropyridine, 0.33 g of N,N-tetramethylenethiocarbamoylsulphenamide and 0.6 g of potassium tert.-butylate following the same procedure as in Example 2; the yield is 0.28 g (75%).

Example 7

Preparation of N-phenyl-5-nitro-2- and -3-thienylamine:

2.9 g of 2-nitrothiophene and 4 g of N-phenylbenzenesulphenamide, dissolved in 10 ml of dimethylformamide, are added dropwise to a stirred solution of 6 g of potassium tert.-butylate in 60 ml of dimethylformamide, while the temperature is kept at about $-20°$ C. The mixture is stirred for a further 15 minutes; then an excess of dilute hydrochloric acid is added to the mixture, after which it is treated in the same way as described in Example 1. The crude product is separated by column chromatography; N-phenyl-5-nitro-2-thienylamine (melting point 186° C., yield 1.8 g, 42%) and N-phenyl-2-nitro-3-thienylamine (melting point 105° C., yield 0.7 g, 15%) are obtained.

Example 8

Preparation of 4-nitro-2-trifluoromethylaniline

A solution of 3.82 g (0.02 mol) of 3-trifluoromethylnitrobenzene, 3.3 g (0.02 mol) of N,N-diethylthiocarbamoylsulphenamide and 0.8 ml (0.02 mol) of methanol in 15 ml of dimethylformamide was added dropwise to a stirred suspension of 4 g (0.1 mol) of sodium hydroxide in 40 ml of dry liquid ammonia.

During the addition the mixture was cooled externally to ensure only slight refluxing of ammonia. After the addition was complete (after 10 minutes) the mixture was stirred at $-30°$ to $-33°$ C. for 6 hours and ammonia was evaporated until the temperature of the mixture reached 0° C. The mixture was then cooled to −10° C. and 120 ml of water were added dropwise while keeping the temperature below +15° C. 3 ml of light petroleum were added to protect the mixture from exposure to air and the whole mixture was then stirred for 15 mins. and left to stand overnight.

The precipitate was filtered and air-dried to give 3.5 g (85%) of the product which had a melting point of 85°–89° C. It consisted of 92–93% of the required 4-nitro-2-trifluoromethylaniline which was contaminated with 4-nitro-3-trifluoromethylaniline produced from the 2-trifluoromethylnitrobenzene which had contaminated the starting material. According to $^1$H-NMR (200 MHz) the product contained less than 1% of the disulphide.

The aqueous filtrate was added dropwise to a stirred mixture comprising 20 ml of 25% aqueous ammonina and 23 ml of 0.95N NaOCl at −12° to −15° C. over a period of 20 mins. After subsequent stirring for 30 mins. at the same temperature the solid was filtered off, dissolved in methylene chloride, the solution was dried with anhydrous $Na_2SO_4$ and the solvent was evaporated to give 2.8 g of N,N-diethylthiocarbamoylsulphenamide (85%) in the form of a solidifying oil.

Similar results were obtained using N,N-dimethylthiocarbamoylsulphenamide.

We claim:

1. Process for the preparation of aromatic amines of the formula

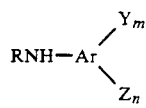

wherein
Ar denotes a mono- or polycyclic aromatic radical with 4 to 16 C atoms which can also contain 1 to 2 hetero atoms from the group consisting of nitrogen, oxygen and sulphur, R denotes hydrogen, $C_1$–$C_4$-alkyl(optionally substituted by halogen or $C_1$–$C_4$-alkoxy), $C_1$–$C_4$-alkenyl, $C_5$–$C_{12}$-cycloalkyl, $C_5$–$C_{12}$-aryl(optionally substituted by halogen, $C_1$–$C_4$-alkyl or $C_1$–$C_4$-alkoxy), Y denotes nitro in the 2- or 4-position in relation to the amino group —NHR, Z denotes halogen, cyano, optionally halogenated $C_1$–$C_4$-alkyl, $C_1$–$C_4$-alkoxy, optionally halogenated $C_1$–$C_4$-alkylmercapto, di-$C_1$–$C_4$-alkylamino, $C_1$–$C_4$-alkylsulphonyl, carboxyl or hydroxyl and m denotes 1 or 2 and n denotes zero or 1, which comprises reacting compounds of the formula

wherein
Y denotes nitro and the remaining symbols have the abovementioned meaning, with organic sulphenamides in aprotic organic solvents or in liquid ammonia in the presence of bases at temperatures of −50° to +100° C., the bases being used in a quantity of 2 to 7 mols per mol of starting compound (II).

2. Process according to claim 1, wherein the starting compounds (II) and the sulphenamides are reacted in a molar ratio of 0.8 to 1.2.

3. Process according to claim 1, wherein R denotes $C_1$–$C_4$-alkyl (optionally substituted by halogen or $C_1$–$C_4$-alkoxy), $C_1$–$C_4$-alkenyl, $C_5$–$C_{12}$-cycloalkyl, $C_5$–$C_{12}$-aryl (optionally substituted by halogen, $C_1$–$C_4$-alkyl or $C_1$–$C_4$-alkoxy), or $C_2$–$C_6$-acyl.

4. Process according to claim 1, wherein R denotes $C_1$–$C_4$-alkyl optionally substituted by halogen or $C_1$–$C_4$-alkoxy or denotes $C_5$–$C_{12}$-aryl optionally substituted by halogen, $C_1$–$C_4$-alkyl or $C_1$–$C_4$-alkoxy.

* * * * *